(12) United States Patent
Jeong et al.

(10) Patent No.: US 7,397,557 B2
(45) Date of Patent: Jul. 8, 2008

(54) SERRATED FOURIER FILTERS AND INSPECTION SYSTEMS

(75) Inventors: Hwan J. Jeong, Los Altos, CA (US); Andrew V. Hill, San Jose, CA (US); Mark S. Wang, San Jose, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 386 days.

(21) Appl. No.: 11/145,873

(22) Filed: Jun. 6, 2005

(65) Prior Publication Data

US 2006/0274305 A1 Dec. 7, 2006

(51) Int. Cl.
*G01N 21/00* (2006.01)
*G02B 27/46* (2006.01)

(52) U.S. Cl. ................. 356/237.5; 356/237.4; 359/559

(58) Field of Classification Search ........................ None
See application file for complete search history.

(56) References Cited

U.S. PATENT DOCUMENTS 3,597,069 A * 8/1971 Heinonen, Jr. ............ 359/563
6,717,661 B1 * 4/2004 Bernstein et al. .......... 356/605
6,940,609 B2 * 9/2005 Scheiner .................... 356/605
7,184,138 B1 * 2/2007 Li ............................. 356/237.2

* cited by examiner

*Primary Examiner*—Gregory J. Toatley, Jr.
*Assistant Examiner*—Juan D Valentin
(74) *Attorney, Agent, or Firm*—Baker & McKenzie LLP (57) ABSTRACT

Serrated Fourier filters and inspection systems are provided. One Fourier filter includes one or more blocking elements configured to block a portion of light from a wafer. The Fourier filter also includes periodic serrations formed on edges of the one or more blocking elements. The periodic serrations define a transition region of the one or more blocking elements. The periodic serrations are configured to vary transmission across the transition region such that variations in the transmission across the transition region are substantially smooth. One inspection system includes a Fourier filter configured as described above and a detector that is configured to detect light transmitted by the Fourier filter. Signals generated by the detector can be used to detect the defects on the wafer.

21 Claims, 8 Drawing Sheets

SERRATED FOURIER FILTERS AND INSPECTION SYSTEMS

BACKGROUND OF THE INVENTION

1. Field of the Invention

This invention generally relates to serrated Fourier filters and inspection systems. Certain embodiments relate to a Fourier filter that includes periodic serrations, which are formed on edges of one or more blocking elements, and which are configured to increase smoothness of transmission variations across a transition region of the one or more blocking elements.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as integrated circuits. However, as the dimensions of semiconductor devices decrease, inspection becomes even more important to the successful manufacture of acceptable semiconductor devices because smaller defects can cause the device to fail. For instance, as the dimensions of semiconductor devices decrease, detection of defects of decreasing size has become necessary since even relatively small defects may cause unwanted aberrations in the semiconductor devices.

Many different types of inspection tools have been developed for the inspection of semiconductor wafers. The inspection tools may be categorized generally according to the types of specimen that they are designed to inspect. For example, one category of inspection tools is generally designed to inspect unpatterned semiconductor wafers. Since these tools are optimized for inspecting unpatterned wafers, these tools are generally not capable of inspecting patterned wafers for a number of reasons. For example, many unpatterned wafer inspection tools are configured such that all of the light collected by a lens or another collector is directed to a single detector that generates a single output signal representative of all of the light collected by the lens. Therefore, light scattered from patterns or other features on the specimen will be combined with other scattered light. As such, the single detector may become saturated and consequently will not yield signals that can be analyzed for defect detection. In addition, even if the single detector does not become saturated, the light scattered from patterns or other features on the wafer can not be separated from other scattered light thereby hindering, if not preventing, defect detection based on the other scattered light.

Patterned wafer inspection is of particular interest and importance to the semiconductor industry because processed semiconductor wafers usually have a pattern of features formed thereon. Although inspection of unpatterned wafers, or "monitor wafers," which have been run through a process tool, may be used as a gauge for the number and types of defects that may be found on patterned wafers, or "product wafers," defects detected on monitor wafers do not always accurately reflect the defects that are detected on patterned wafers after the same process in the process tool. Inspection of patterned wafers after such processing is, therefore, important to accurately detect defects that may have been formed on the wafer during, or as a result of, processing. Therefore, inspecting patterned wafers or product wafers may provide more accurate monitoring and control of processes and process tools than inspection of monitor wafers.

Many inspection tools have been developed for patterned wafer inspection. For example, one patterned wafer inspection tool utilizes spatial filters to separate light scattered from patterned features from other scattered light such that the other scattered light may be separately detected. Since the light scattered from patterned features depends on various characteristics of the patterned features such as lateral dimension and period, the design of the spatial filter also depends on such characteristics of the patterned features. As a result, the spatial filter must be designed based on known or determined characteristics of the patterned features and must vary as different patterned features are being inspected.

One type of spatial filter that may be used as described above is a Fourier filter. Fourier filters are relatively useful for filtering light from patterned features formed on a wafer. However, Fourier filters can have adverse effects on the transmitted light because the filters can diffract desirable light into undesirable directions. To reduce the adverse effects of a Fourier filter on the transmitted light, the transition between the blocking area and the transparent area of the Fourier filter should be relatively smooth without introducing phase change to the transmitted light.

A number of different approaches have been proposed to increase the smoothness of the transition from the blocking to transparent areas of Fourier filters. One approach is to form a blocking area of a Fourier filter on a glass plate with 100% opaqueness at the center of the blocking area with a gradual transition to 100% transmission at the edges. This kind of Fourier filter can perform well as long as it is made correctly. However, fabricating this kind of filter is not only expensive but also technically challenging. Another approach is to introduce random serrations on the edges of otherwise 100% opaque blocking elements of a Fourier filter. Fourier filters made in this manner are relatively inexpensive but do not provide the desired performance.

Accordingly, it would be advantageous to develop a Fourier filter that has a relatively smooth transition between blocking and transmission areas thereby providing relatively good performance and that is relatively inexpensive and easy, technically speaking, to manufacture.

SUMMARY OF THE INVENTION

The following description of various embodiments of serrated Fourier filters and inspection systems is not to be construed in any way as limiting the subject matter of the appended claims.

One embodiment relates to a Fourier filter configured to block a portion of light from a wafer. The Fourier filter includes one or more blocking elements configured to block the portion of the light. The Fourier filter also includes periodic serrations formed on edges of the one or more blocking elements. The periodic serrations define a transition region of the one or more blocking elements. The periodic serrations are configured to vary transmission across the transition region such that variations in the transmission across the transition region are substantially smooth.

In one embodiment, a period of the periodic serrations is selected such that all diffraction orders other than zeroth order are directed outside of photosensitive elements at an image plane. In some embodiments, the periodic serrations are configured to substantially reduce diffraction of zeroth order light into neighboring photosensitive elements (e.g., pixels of a detector) at an image plane. In a further embodiment, the periodic serrations are configured to prevent a substantial reduction in the signal-to-noise ratio of light transmitted by the Fourier filter.

In one embodiment, the transmission is an average transmission. In another embodiment, the variations in the transmission include one or more local transmission minima.

In some embodiments, a width of the periodic serrations varies approximately sinusoidally across a length of the periodic serrations. In other embodiments, a width of the periodic serrations varies approximately linearly across a length of the periodic serrations. In an additional embodiment, the periodic serrations are arranged symmetrically along the edges of the one or more blocking elements. In different embodiments, the periodic serrations are arranged asymmetrically along the edges of the one or more blocking elements. Each of the embodiments of the Fourier filter described above may be further configured as described herein.

Another embodiment relates to another Fourier filter that is configured to block a portion of light from a wafer. This Fourier filter includes one or more blocking elements configured to block the portion of the light. The one or more blocking elements have a transition region across which transmission varies. The transition region is not physically smooth. However, the transition region is substantially optically smooth. This embodiment of a Fourier filter may be further configured as described herein.

An additional embodiment relates to an inspection system configured to detect defects on a wafer. The system includes a Fourier filter that includes periodic serrations formed on edges of one or more blocking elements. The one or more blocking elements are configured to block a portion of light returned from the wafer. The periodic serrations define a transition region of the one or more blocking elements. The periodic serrations are configured to vary transmission across the transition region such that variations in the transmission across the transition region are substantially smooth. The system also includes a detector that is configured to detect light transmitted by the Fourier filter. Signals generated by the detector can be used to detect the defects on the wafer.

In one embodiment, a period of the periodic serrations is selected such that all diffraction orders other than zeroth order are directed outside of photosensitive elements of the detector. In an additional embodiment, the periodic serrations are configured to substantially reduce diffraction of zeroth order light into neighboring photosensitive elements (e.g., pixels) of the detector. In some embodiments, the periodic serrations are configured to prevent a substantial reduction in the signal-to-noise ratio of the light transmitted by the Fourier filter.

In one embodiment, the transmission is an average transmission. In another embodiment, the variations in the transmission include one or more local transmission minima.

In some embodiments, a width of the periodic serrations varies approximately sinusoidally across a length of the periodic serrations. In other embodiments, a width of the periodic serrations varies approximately linearly across a length of the periodic serrations. In another embodiment, the periodic serrations are arranged symmetrically along the edges of the one or more blocking elements. In a different embodiment, the periodic serrations are arranged asymmetrically along the edges of the one or more blocking elements. Each of the embodiments of the inspection system described above may be further configured as described herein.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities. A wafer may include one or more layers formed upon a substrate. For example, such layers may include, but are not limited to, a resist, a dielectric material, and a conductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Figure 1:
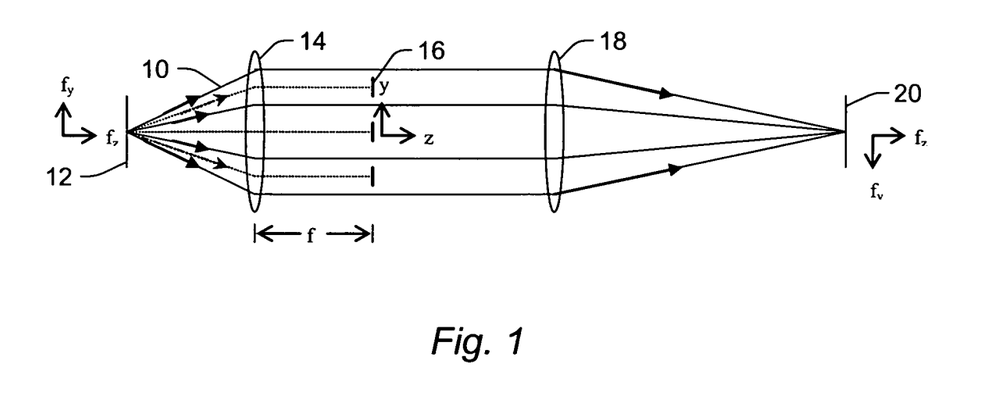
FIG. 1 is a schematic diagram illustrating a side view of one example of a system that includes a Fourier filter.

FIG. 1 illustrates one example of an imaging system that includes a Fourier filter. As shown in FIG. 1, light 10 from object 12 is collected by collection lens 14. Object 12 may be, for example, a wafer. Collection lens 14 may include any suitable refractive or reflective lens known in the art. Light 10 generally includes scattered and diffracted light. Light collected by collection lens 14 passes through a Fourier plane of the imaging system at which Fourier filter 16 is positioned. Fourier filter 16 may be configured as described herein. Light that passes through the Fourier filter is focused by imaging lens 18 on image plane 20 at which a detector (not shown) may be positioned. The imaging lens may include any appropriate refractive or reflective lens known in the art. The detector may include any appropriate detector known in the art. For example, the detector may include a 1-dimensional array of photosensitive elements such as image sensors or pixels.

A Fourier filter can be generally defined as a light blocking apparatus that blocks undesirable light at a Fourier plane of an optical system. A Fourier filter is especially useful in blocking diffracted light from repetitive pattern features on an object such as a wafer because the light diffracted from such features is discrete and well confined spatially at the Fourier plane. However, a Fourier filter can also produce adverse effects on the light transmitted through the Fourier filter because it can also diffract desirable light into undesirable directions. To reduce the adverse effects of a Fourier filter on the transmitted light, the transition between a blocking area and a transparent area in the Fourier filter should be substantially smooth without introducing phase change in the transmitted light. However, achieving this kind of smooth transition physically is expensive in the optical frequency range. Fortunately, optics do not necessarily require a physically smooth transition in order to be optically smooth. In particular, as long as the transition is substantially smooth in an optical sense, it makes no difference in performance if the transition is or is not physically smooth. The embodiments described herein provide an inexpensive Fourier filter that is easy to manufacture and that has a transition region that is substantially smooth optically but not necessarily smooth physically.

Accordingly, one embodiment of a Fourier filter that is configured to block a portion of light from a wafer includes one or more blocking elements that are configured to block the portion of the light. The one or more blocking elements have a transition region across which transmission varies. The transition region is not physically smooth. However, the transition region is substantially optically smooth. This embodiment of the Fourier filter may be further configured as described herein and shown in FIGS. 3, 5, and 6.

Another embodiment of a Fourier filter that is configured to block a portion of light from a wafer includes one or more blocking elements configured to block the portion of the light. The Fourier filter also includes periodic serrations formed on edges of the one or more blocking elements. The periodic serrations define a transition region of the one or more blocking elements. The periodic serrations are configured to vary transmission across the transition region such that variations in the transmission across the transition region are substantially smooth. This embodiment of a Fourier filter may be further configured as described herein and shown in FIGS. 3, 5, and 6.

In this manner, the Fourier filter has periodic serrations along the edges of the blocking element(s) to make the transition from opaque to 100% transmission substantially smooth. The transmission may be an average transmission. In addition, the Fourier filter may include any edge serration pattern whose average transmission varies substantially smoothly from 0% transmission to 100% transmission. The Fourier filter may also include any serration pattern whose transmission patterns vary substantially smoothly from 0% transmission to 100% transmission with one or more local transmission minima in between. In this manner, the variations in the transmission across the transition region may include one or more local transmission minima. In other words, although the transmission may vary substantially smoothly from 0% transmission to 100% transmission, the transmission may or may not vary monotonically.

Accordingly, the Fourier filter includes periodic, rather than random, serrations on the edges of, an otherwise opaque, Fourier filter. Periodic serrations soften the edges of the blocking element(s) but diffract light into discrete orders. However, the diffraction from periodic serrations is not random but forms discrete diffraction orders at the image plane due to the periodicity of the serrations, and consequently all of the diffracted light can be directed outside of the detection area by making the serration period fine enough. In one embodiment, therefore, a period of the periodic serrations is selected such that all diffraction orders other than zeroth order are directed outside of photosensitive elements at an image plane. In this manner, only the zeroth order, undiffracted light, can reach the detector. The undiffracted light does not "see" the details of the periodic serrations but experiences only a smooth transition provided by the average transmission of the periodic serrations. The following theory will show this effect clearly. Thus, a Fourier filter with periodic serrations is optically equivalent to a smoothly graded Fourier filter described further above but is much easier to fabricate.

Theoretical description of serrated Fourier filters provided herein uses the following coordinate system. In particular, the illumination line and detector are arranged to extend lengthwise along the y-direction. Fourier filters are positioned to extend lengthwise in the x-direction. xy coordinates are set in the Fourier plane. $f_x, f_y$ coordinates are set at wafer and detector planes. $f_x$ or $f_y$=(Physical dimension)/$\lambda f$, where f=focal length. This coordinate system is illustrated in FIG. 1.

Figure 2:
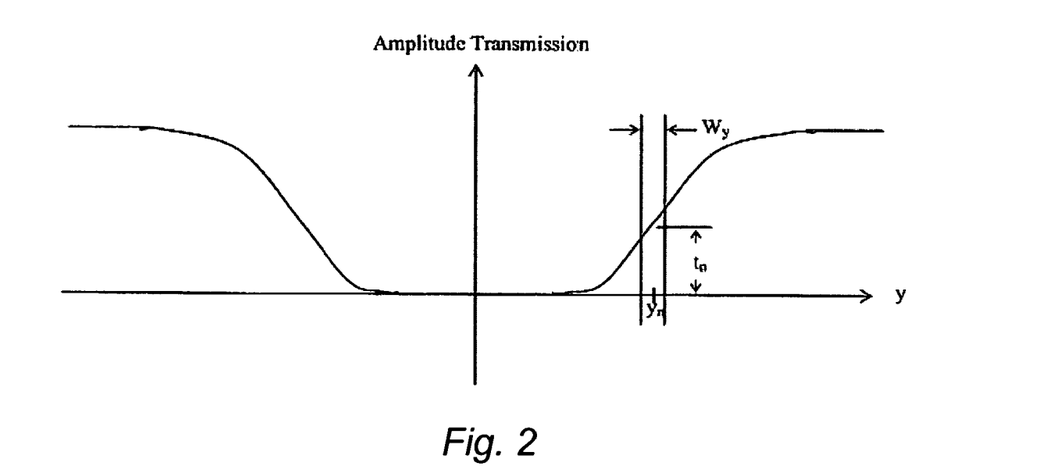
FIG. 2 is a plot illustrating amplitude transmission of a graded Fourier filter.

One example of the amplitude transmission of a general graded Fourier filter is shown in FIG. 2. The Fourier filter is graded in the sense that it has 100% opaqueness at the center of a blocking element, which gradually transitions to 100% transmission at the edges of the blocking element. The transition in transmission is provided by gradual transitions in the physical properties of the blocking element. These transmission characteristics are shown in FIG. 2 by the low amplitude transmission proximate to the center of the amplitude transmission plot, which corresponds to the 100% opaqueness of the blocking element. The transition regions of the Fourier filter are shown by the increases in amplitude transmission from the 100% opaqueness to the high amplitude transmission areas of the Fourier filter at the edges of the plot. These high amplitude transmission areas correspond to the 100% transmission at the edges of the blocking element. The amplitude transmission is described by the following equation:

$$\sum_n t_n rect\left(\frac{y-y_n}{w_y}\right) \qquad (1)$$

where $t_n$=amplitude transmission, not intensity transmission. $y_n$ and $w_y$ are illustrated in FIG. 2. The diffraction pattern of a filter is the same as its Fourier transform. The Fourier transform of equation (1) is:

$$w_y \sum_n t_n \sin c(w_y f_y)\exp(-j2\pi y_n f_y). \qquad (2)$$

Figure 3:
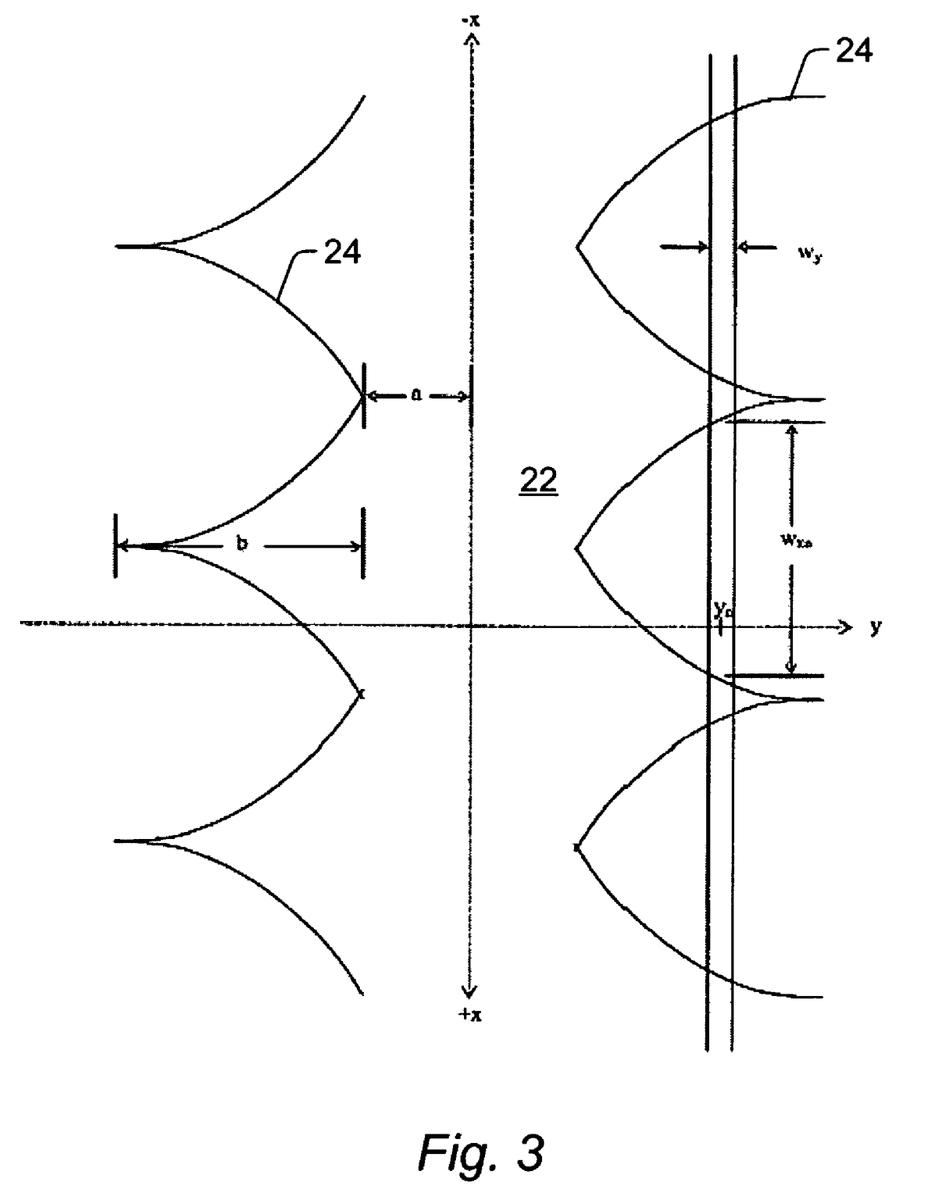
FIG. 3 is a schematic diagram illustrating a top view of one embodiment of a Fourier filter that includes periodic serrations.

One embodiment of a "serrated Fourier filter" is illustrated in FIG. 3. As shown in FIG. 3, the serrated Fourier filter includes blocking element 22 that is configured to block a portion of the light from a wafer. The serrated Fourier filter also includes periodic serrations 24 formed on edges of blocking element 22. Periodic serrations 24 define a transition region of blocking element 22. Periodic serrations 24 are configured to vary transmission across the transition region such that variations in the transmission across the transition region are substantially smooth. This embodiment of a Fourier filter may be further configured as described herein.

Although a particular number of periodic serrations are shown in FIG. 3 and other figures described herein, it is to be understood that the number of periodic serrations formed on the edges of the blocking element(s) of the Fourier filter will vary depending on, for example, the pitch of the periodic serrations and the length of the blocking elements. The pitch of the periodic serrations may be selected as described further herein. In addition, although a portion of one blocking element is shown in FIG. 3 and other figures described herein, it is to be understood that the Fourier filter may include more than one blocking element.

In general, a serrated Fourier filter can be described by the following equation:

$$\sum_n rect\left(\frac{y-y_n}{w_y}\right)rect\left(\frac{x}{w_{xn}}\right)\otimes \frac{1}{p}comb\left(\frac{x}{p}\right); \text{ Variables separated.} \qquad (3)$$

The variables of equation (3) are illustrated in FIG. 3. The Fourier transform of equation (3) is:

$$w_y \sum_n \sin c(w_y f_y)\exp(-j2\pi y_n f_y)w_{xn}\sin c(w_{xn} f_x)comb(pf_x). \qquad (4)$$

Figure 4:
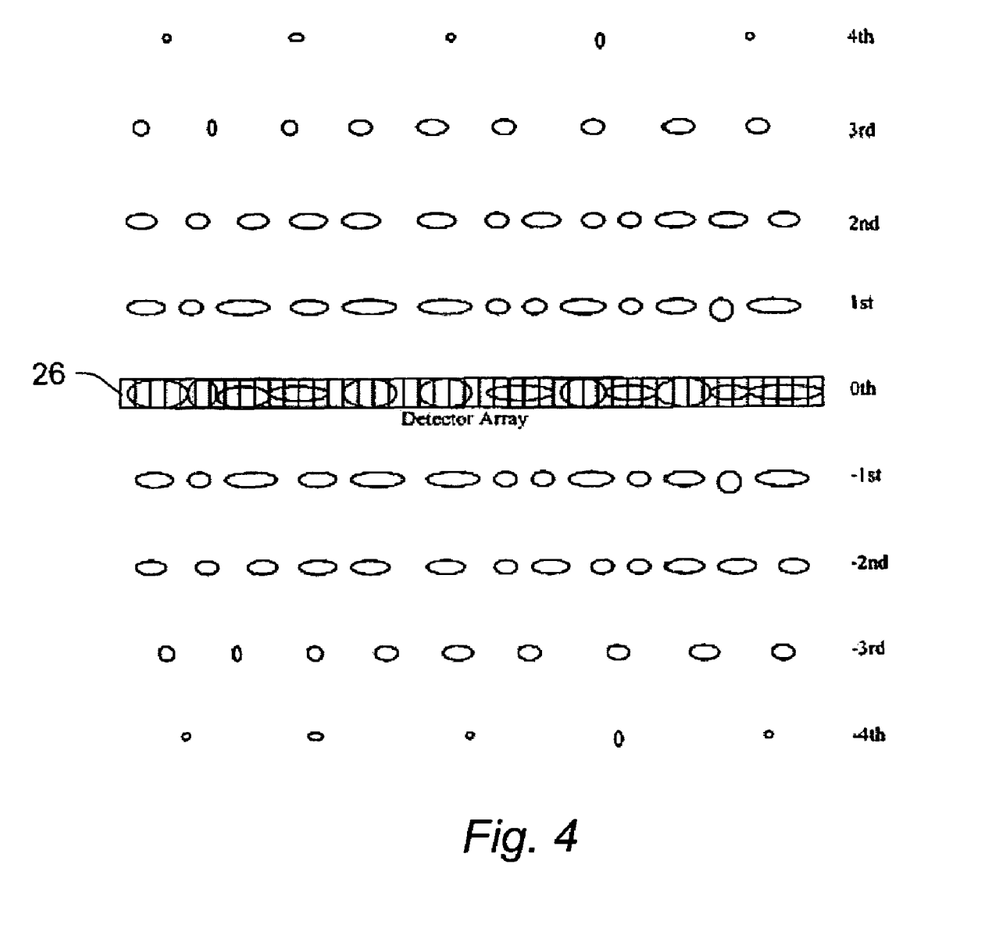
FIG. 4 is a schematic diagram illustrating a diffraction pattern of one embodiment of a Fourier filter that includes periodic serrations.

Diffraction by the serrated Fourier filter in the x-direction is shown in FIG. 4, which illustrates the diffraction pattern of a serrated Fourier filter. As shown in FIG. 4, zeroth order light is incident on detector array 26. In addition, as shown in FIG. 4, only zeroth order light is incident on detector array 26. All other orders of the light diffracted by the serrated Fourier filter are not incident on detector array 26. In this manner, a Fourier filter with periodically serrated edges diffracts light out of a sensor array except zeroth order light. Detector array 26 may include any suitable detector known in the art.

The zeroth order part of equation (4) is:

$$w_y \sum_n w_{xn}\sin c(w_y f_y)\exp(-j2\pi y_n f_y) \qquad (5)$$

which is the same as equation (2). It is noted that there is a one-to-one correspondence between $t_n$ and $w_{xn}$. That is, serrated Fourier filters are substantially equivalent to graded Fourier filters when only the zeroth order is selected. The inverse Fourier transform of equation (5) is:

$$\sum_n w_{xn}rect\left(\frac{y-y_n}{w_y}\right) \qquad (6)$$

which is the same as the function for a graded Fourier filter as shown in equation (1). It is noted that all of the above equations can be presented mathematically more elegantly in integral form by taking the limits of $w_x \to 0$ and $w_y \to 0$. However, the present form is better suited for numerical calculation of diffraction patterns.

The diffraction speckle size at the Fourier plane can be described by the following equation:

$$d_x \approx \frac{\lambda f}{w_L} \qquad (7)$$

where $d_x$=speckle length at the Fourier plane along the Fourier filter (along the length of the Fourier filter, which is arranged in the x-direction), $\lambda$=wavelength, f=focal length of front lens group (e.g., collection lens 14 shown in FIG. 1), and $w_L$=illumination line width at the object plane. The length of the illumination line is arranged in the y-direction.

The serration pitch of a serrated Fourier filter can be determined from the following equation:

$$p << d_x \approx \frac{\lambda f}{w_L} \qquad (8)$$

where p=pitch of serration. In addition, the pitch of the periodic serrations may be selected such that the first order diffraction is out of the illuminated line on the detector array. In this manner, a Fourier filter with periodically serrated edges may be configured to have a serration period that is small enough to diffract all diffraction orders except zeroth order light out of the sensor region. In other words, $$\frac{\lambda f}{p} > w_L. \qquad (9)$$

Equations (8) and (9) are equivalent. Any kind of periodic serration having a serration pitch that meets equation (8) or (9) can be used to provide a high performance Fourier filter.

The following analysis provides examples of different periodically serrated Fourier filter embodiments. However, it is to be understood that the embodiments described herein are not limited to the examples presented in this disclosure. In particular, any variation of a serrated filter that is optically equivalent to those described herein can be used to provide high performance Fourier filtering. One such example is a threaded rod.

The amplitude transmission of a graded (unserrated) Fourier filter can be described by the following equation:

$$\sum_n t_n \left[ rect\left(\frac{y+y_n+y_0}{w_y}\right) + rect\left(\frac{y-y_n-y_0}{w_y}\right) \right] \quad (10)$$

where $t_n$=transmission at nth slice of the graded filter. The Fourier transform of equation (10) is:

$$= 2w_y \sum_n t_n \text{sinc}(w_y f_y) \cos(2\pi(y_n+y_0)f_y). \quad (11)$$

Figure 5:
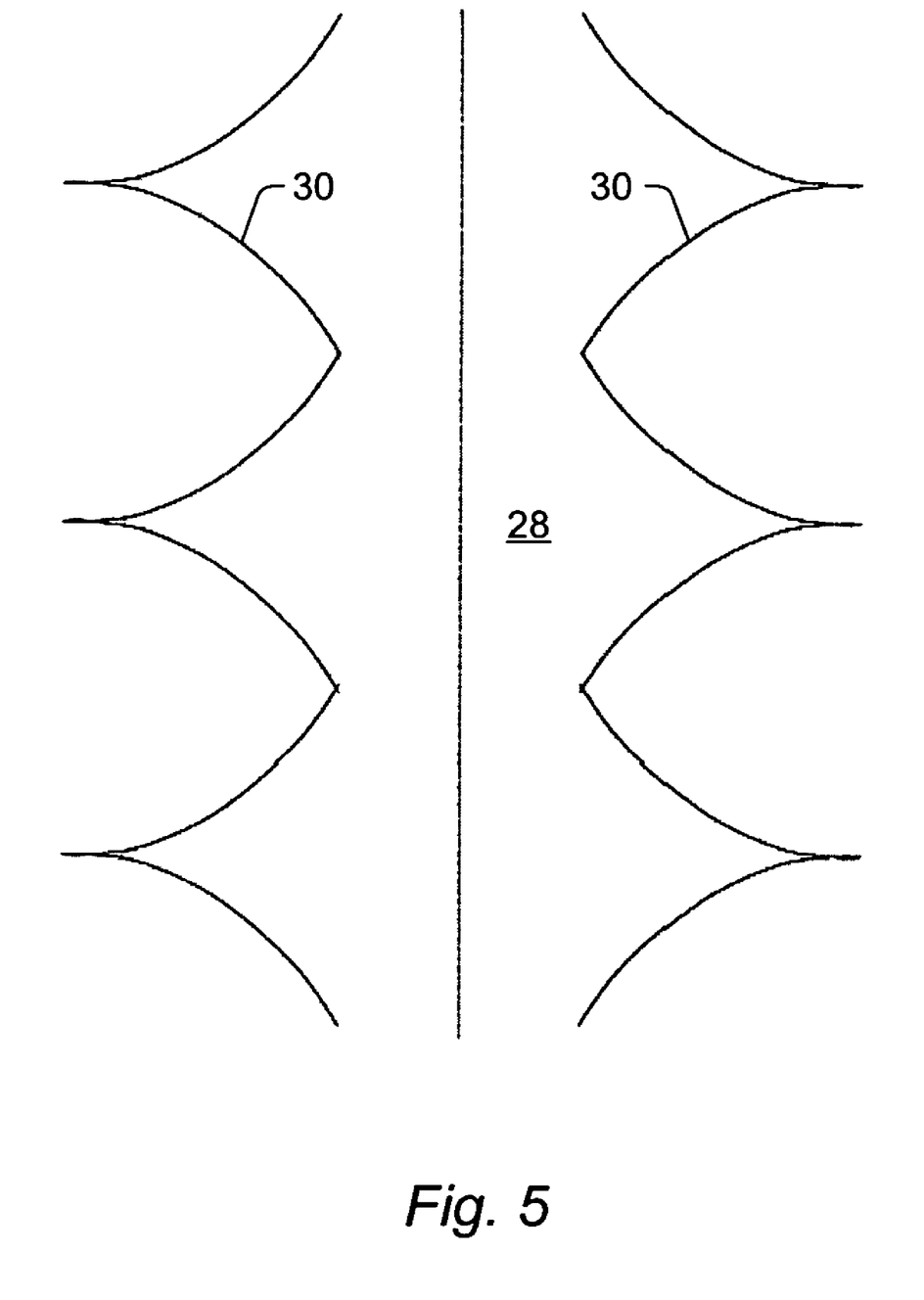
FIGS. 5-6 are schematic diagrams illustrating a top view of different embodiments of a Fourier filter that includes periodic serrations.

In one embodiment, a periodically serrated Fourier filter may be symmetrically serrated. In other words, the periodic serrations of such a Fourier filter may be arranged symmetrically along the edges of one or more blocking elements of the Fourier filter. In this manner, a symmetrically serrated Fourier filter includes periodic serrations on the edges of the blocking element(s) of the Fourier filter that have folding symmetry, as shown in FIG. 5. As shown in FIG. 5, in this embodiment, the serrated Fourier filter includes blocking element 28 that is configured to block a portion of the light from a wafer. The serrated Fourier filter also includes periodic serrations 30 formed on edges of blocking element 28. Periodic serrations 30 define a transition region of blocking element 28. Periodic serrations 30 are configured to vary transmission across the transition region such that variations in the transmission across the transition region are substantially smooth. This embodiment of a Fourier filter may be further configured as described herein.

The general expression of a symmetrically periodically serrated Fourier filter is described by the following equation:

$$\sum_n \left[ rect\left(\frac{y+y_n+y_0}{w_y}\right) + rect\left(\frac{y-y_n-y_0}{w_y}\right) \right] rect\left(\frac{x}{w_{xn}}\right) \otimes \frac{1}{p} comb\left(\frac{x}{p}\right) \quad (12)$$

The variables in this equation are illustrated in FIG. 3. The Fourier transform of equation (12) is:

$$2w_y \sum_n \text{sinc}(w_y f_y) \cos(2\pi(y_n+y_0)f_y) w_{xn} \text{sinc}(w_{xn} f_x) comb(pf_x). \quad (13)$$

The zeroth order part of this equation is:

$$2w_y \sum_n w_{xn} \text{sinc}(w_y f_y) \cos(2\pi(y_n+y_0)f_y). \quad (14)$$

Therefore, only the zeroth diffraction order reaches the image sensor, and all other diffraction orders "miss" the image sensor. Equation (14) is the same as equation (11), if $w_{xn}$ is set to be equal to $t_n$ in equation (11). Thus, here again, the analysis shows that a periodically serrated Fourier filter is substantially optically equivalent to a graded Fourier filter.

The first order part of the Fourier transform for the symmetrically periodically serrated Fourier filter is:

$$2w_y \sum_n w_{xn} \text{sinc}(w_y f_y) \cos(2\pi(y_n+y_0)f_y) \text{sinc}\left(\frac{w_{xn}}{p}\right). \quad (15)$$

Equation (15) can be used to estimate smearing of diffracted light into the sensor region.

In another embodiment, the periodically serrated Fourier filter may be asymmetrically serrated. In such an embodiment, the periodic serrations of the Fourier filter are arranged asymmetrically along the edges of the one or more blocking elements of the Fourier filter. For example, an asymmetrically serrated Fourier filter includes periodic serrations formed on edges of one or more blocking elements of the Fourier filter that may be staggered (e.g., half-period staggered), as shown in FIGS. 3 and 6.

Figure 6:
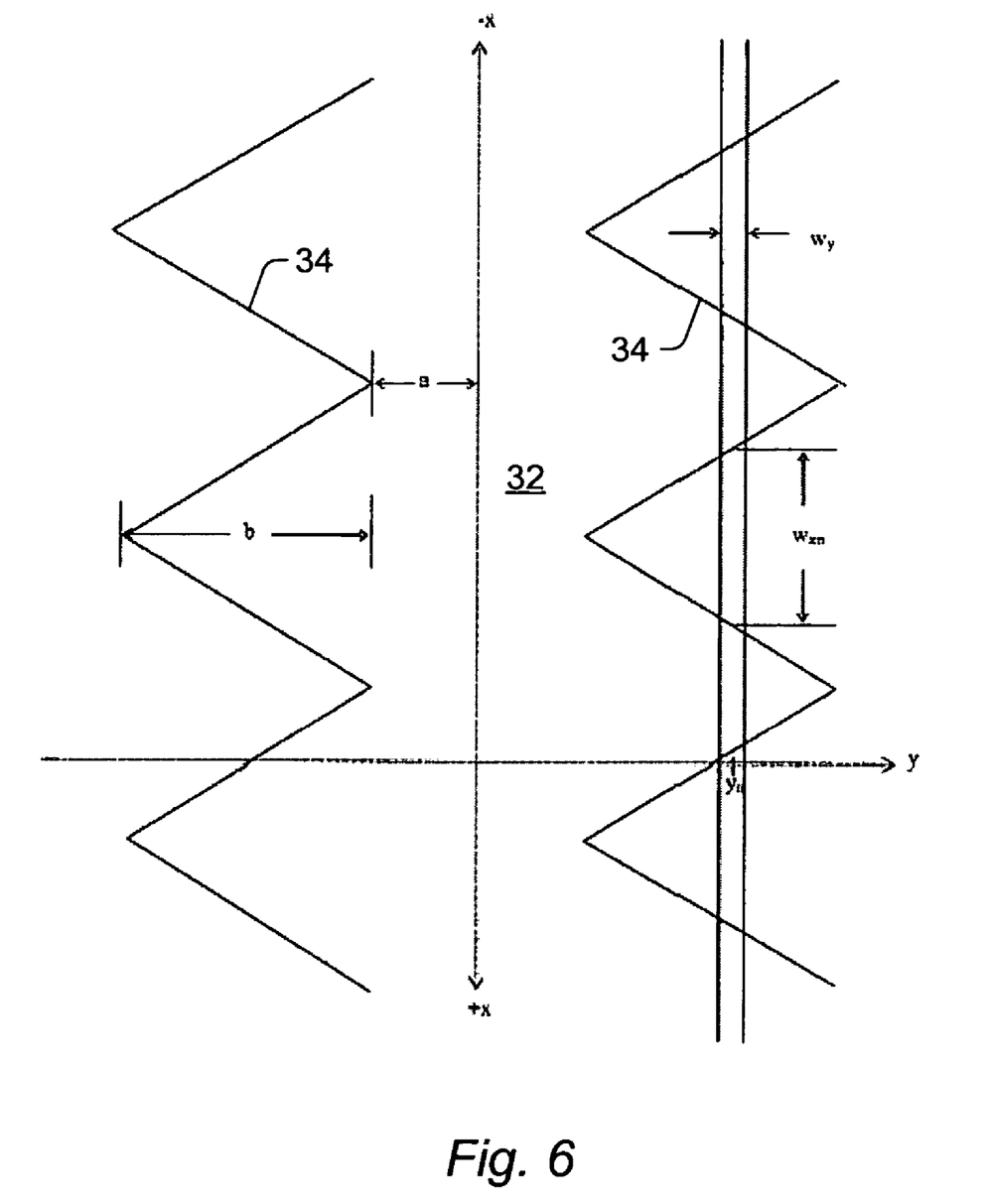

As shown in FIG. 6, in this embodiment, the serrated Fourier filter includes blocking element 32 that is configured to block a portion of the light from a wafer. The serrated Fourier filter also includes periodic serrations 34 formed on edges of blocking element 32. Periodic serrations 34 define a transition region of blocking element 32. Periodic serrations 34 are configured to vary transmission across the transition region such that variations in the transmission across the transition region are substantially smooth. This embodiment of a Fourier filter may be further configured as described herein.

The general expression of an asymmetrically periodically serrated Fourier filter is described by the following equation:

$$\sum_n \left[ \begin{array}{l} rect\left(\frac{y+y_n+y_0}{w_y}\right) rect\left(\frac{x+\frac{p}{4}}{w_{xn}}\right) + \\ rect\left(\frac{y-y_n-y_0}{w_y}\right) rect\left(\frac{x-\frac{p}{4}}{w_{xn}}\right) \end{array} \right] \otimes \frac{1}{p} comb\left(\frac{x}{p}\right). \quad (16)$$

The variables in equation (16) are illustrated in FIGS. 3 and 6. The Fourier transform of equation (16) is:

$$2w_y \sum_n w_{xn} \text{sinc}(w_y f_y) \cos\left( \begin{array}{l} 2\pi(y_n+y_0)f_y + \\ 2\pi\frac{p}{4}f_x \end{array} \right) \text{sinc}(w_{xn} f_x) comb(pf_x). \quad (17)$$

The zeroth order part of this Fourier transform is:

$$2w_y \sum_n w_{xn} \text{sinc}(w_y f_y) \cos(2\pi(y_n+y_0)f_y) \quad (18)$$

which is equivalent to equations (11) and (14). Therefore, an asymmetrically serrated Fourier filter is optically equivalent to both graded and symmetrically serrated Fourier filters. More generally, as long the serrations of the Fourier filter are periodic, and the pitch of the serrations meets equation (8) or (9), all of the periodically serrated Fourier filters are optically equivalent to each other and to a graded Fourier filter.

The first order part of the Fourier transform of FIG. 17 is:

$$-2w_y \sum_n w_{xn} \text{sinc}(w_y f_y) \sin(2\pi(y_n + y_0)f_y) \text{sinc}\left(\frac{w_{xn}}{p}\right). \quad (19)$$

Equation (19) can be used to estimate smearing of diffracted light into the sensor region.

The diffraction pattern of a serrated Fourier filter depends on the shape of the serrations. Several serration shapes are described herein to illustrate how diffraction patterns depend on serration shape. The following serration shapes are provided only as examples of suitable serration shapes. It is to be understood that the embodiments described herein are not limited to the serration shapes presented in this disclosure.

In some embodiments, the periodically serrated Fourier filter may be sinusoidally serrated. In such an embodiment, a width of the periodic serrations of the Fourier filter varies approximately sinusoidally along a length of the periodic serrations. In this manner, sinusoidal serrations have edge lines that depict a part of sinusoidal curve, as shown in FIGS. 3 and 5. As shown in FIGS. 3 and 5, a sinusoidally periodically serrated Fourier filter may be symmetrical or asymmetrical as described further above. This kind of serration is relatively difficult to produce physically because of the infinitely sharp tips of the serrations. However, such serrations provide one of the best optical performances due to its substantially gradual average transmission change. This filter may or may not be practical but will be used as a performance reference. In other words, the performance of a more practical periodically serrated Fourier filter may be assessed by comparing its Fourier transform with that of the sinusoidally periodically serrated Fourier filter.

A sinusoidally serrated Fourier filter has the following energy distribution in its transition region: $2/\pi \approx 63.7\%$ transmitted, $(1-2/\pi) \approx 36.3\%$ absorbed. Among the transmitted energy, 50% goes to the zeroth diffraction order, and $(2/\pi - 0.5) \approx 13.7\%$ goes into higher diffraction orders. 50% of the energy going into the zeroth diffraction order reconfirms that the performance of this filter should be optimum or at least very close to optimum.

Figure 7:
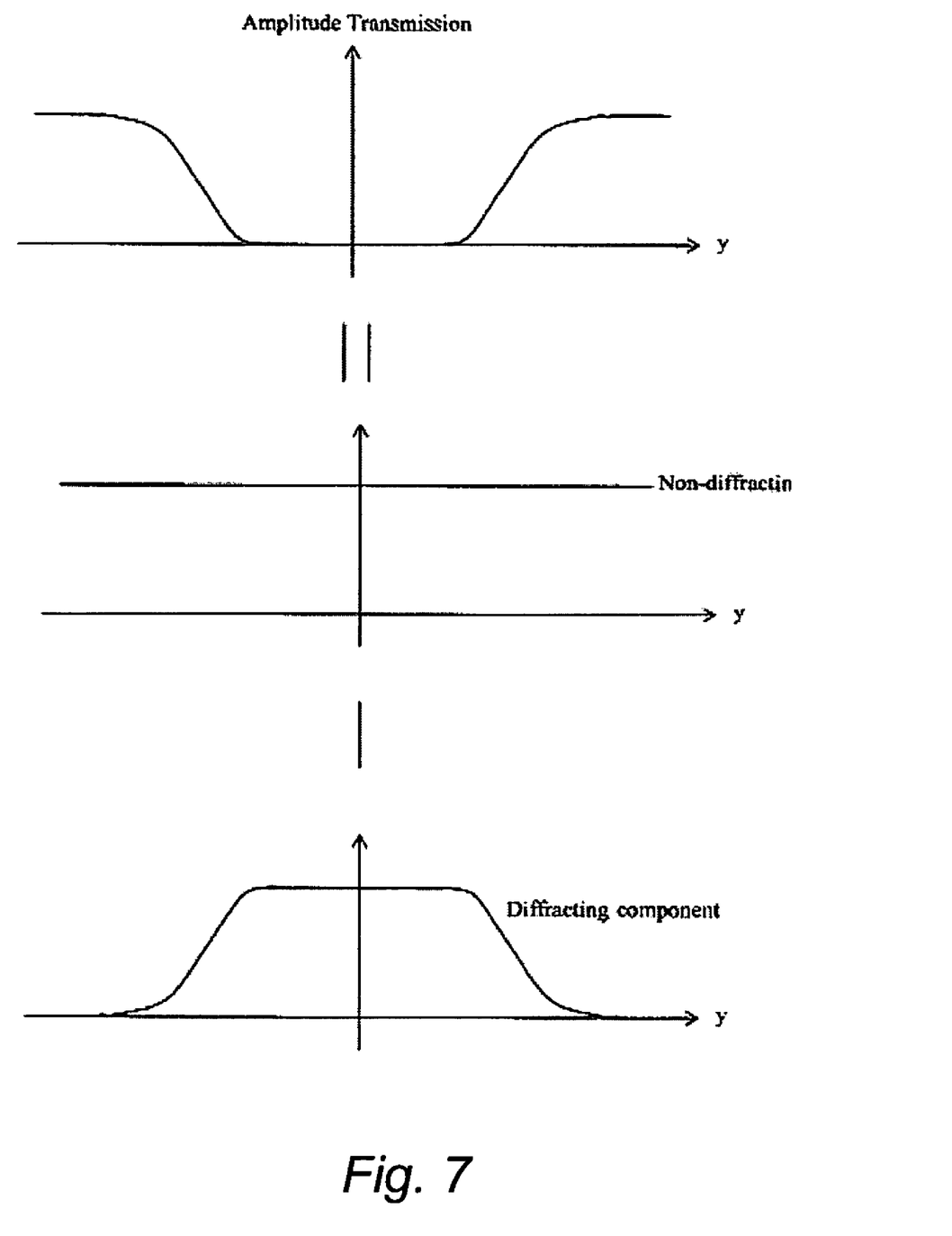
FIG. 7 is a plot illustrating separation of diffracting and non-diffracting components of a Fourier filter.

Diffraction of the sinusoidally serrated Fourier filter can be easily calculated by first separating the non-diffracting component from the whole transmitted wavefront (according to Babinet's principle), as shown in FIG. 7. In particular, as shown in FIG. 7, the non-diffracting component of a Fourier filter can be subtracted from the diffracting component of the Fourier filter to produce the amplitude transmission of the Fourier filter. The middle portions of the plots shown in FIG. 7 correspond to a blocking element of the Fourier filter while the end portions of the plots shown in FIG. 7 correspond to transmission areas of the Fourier filter on both sides of the blocking element. The Fourier transform for a sinusoidally serrated Fourier filter is:

$$= \delta(f_y) - \int_{-a-b}^{-a}\left[1 + \sin\left(\frac{\pi(y+a)}{2b}\right)\right]\exp(-j2\pi f_y y)\,dy - \quad (20)$$

$$\int_{-a}^{a}\exp(-j2\pi f_y y)\,dy - \int_{a}^{a+b}\left[1 - \sin\left(\frac{\pi(y-a)}{2b}\right)\right]\exp(-j2\pi f_y y)\,dy$$

-continued $$= \delta(f_y) - \int_{-a-b}^{-a}\left[1 + \frac{1}{2j}\left(\exp\left(j\frac{\pi(y+a)}{2b}\right) - \exp\left(j\frac{\pi(y+a)}{2b} -\right)\right)\right] \quad (21)$$

$$\exp(-j2\pi f_y y)\,dy - \int_{-a}^{a}\exp(-j2\pi f_y y)\,dy -$$

$$\int_{a}^{a+b}\left[1 - \frac{1}{2j}\left(\exp\left(j\frac{\pi(y-a)}{2b}\right) - \exp\left(j\frac{\pi(y+a)}{2b} -\right)\right)\right]\exp(-j2\pi f_y y)\,dy$$

$$= \delta(f_y) - \int_{a}^{a+b}\left[1 + \frac{1}{2j}\left(\exp\left(j\frac{\pi(-y+a)}{2b}\right) - \exp\left(j\frac{\pi(-y+a)}{2b} -\right)\right)\right] \quad (22)$$

$$\exp(j2\pi f_y y)\,dy - \int_{-a}^{a}\exp(-j2\pi f_y y)\,dy -$$

$$\int_{a}^{a+b}\left[1 - \frac{1}{2j}\left(\exp\left(j\frac{\pi(y-a)}{2b}\right) - \exp\left(j\frac{\pi(y-a)}{2b} -\right)\right)\right]$$

$$\exp(-j2\pi f_y y)\,dy$$

$$= \delta(f_y) - \int_{a}^{a+b}\left[1 + \frac{1}{2j}\left(\exp\left(j\frac{\pi(-y+a)}{2b}\right) - \exp\left(j\frac{\pi(-y+a)}{2b} -\right)\right)\right] \quad (23)$$

$$\exp(j2\pi f_y x)\,dy - \int_{-a}^{a}\exp(-j2\pi f_y y)\,dy -$$

$$\int_{a}^{a+b}\left[1 - \frac{1}{2j}\left(\exp\left(j\frac{\pi(y-a)}{2b}\right) - \exp\left(j\frac{\pi(y-a)}{2b} -\right)\right)\right]$$

$$\exp(-j2\pi f_y y)\,dy$$

$$= \delta(f_y) - \int_{a}^{a+b}\sin\left[2\pi\left(f_y - \frac{1}{4b}\right)y + \frac{2\pi a}{4b}\right]dy + \quad (24)$$

$$\int_{a}^{a+b}\sin\left[2\pi\left(f_y + \frac{1}{4b}\right)y - \frac{2\pi a}{4b}\right]dy -$$

$$2\int_{a}^{a+b}\cos(2\pi f_y y)\,dy - \int_{-a}^{a}\exp(-j2\pi f_y y)\,dy$$

$$= \delta(f_y) + \frac{1}{2\pi\left(f_y - \frac{1}{4b}\right)}\left[\cos\left(2\pi(a+b)f_y - \frac{\pi}{2}\right) - \cos(2\pi a f_y)\right] - \quad (25)$$

$$\frac{1}{2\pi\left(f_y + \frac{1}{4b}\right)}\left[\cos\left(2\pi(a+b)f_y + \frac{\pi}{2}\right) - \cos(2\pi a f_y)\right] -$$

$$\frac{1}{\pi f_y}\sin(2\pi(a+b)f_y)$$

$$= \delta(f_x) + \frac{1}{2\pi\left(f_x - \frac{1}{4b}\right)}[\sin(2\pi(a+b)f_x) - \cos(2\pi a f_x)] + \quad (26)$$

$$\frac{1}{2\pi\left(f_x + \frac{1}{4b}\right)}[\sin(2\pi(a+b)f_x) + \cos(2\pi a f_x)] - \frac{1}{\pi f_x}\sin(2\pi(a+b)f_x)$$

$$= \delta(f_y) - \quad (27)$$

$$\frac{1}{(1-4bf_y)(1+4bf_y)}\left[2(a+b)\frac{\sin(2\pi(a+b)f_y)}{2\pi(a+b)f_y} - \frac{4b}{\pi}\cos(2\pi a f_y)\right]$$

$$= \delta(f_y) - \quad (28)$$

$$\frac{1}{(1-4bf_y)(1+4bf_y)}\left[2(a+b)\text{sinc}(2(a+b)f_y) - \frac{4b}{\pi}\cos(2\pi a f_y)\right]$$

$$\approx \begin{cases} \delta(f_y) - \frac{1}{(1-4bf_y)(1+4bf_y)}\left[2b\text{sinc}(2bf_y) - \frac{4b}{\pi}\right] & \text{as } a \to 0 \\ \delta(f_y) - 2a\text{sinc}(2af_y) & \text{as } b \to 0 \end{cases} \quad (29)$$

In another embodiment, the periodically serrated Fourier filter may be a linearly serrated Fourier filter. In such an embodiment, a width of the periodic serrations of the Fourier filter varies approximately linearly across a length of the periodic serrations. In this manner, a linearly serrated Fourier filter includes serrated edges that are a zigzag of straight lines, as shown in FIG. 6. As shown in FIG. 6, the linearly serrated Fourier filter may be an asymmetrically serrated Fourier filter. Alternatively, a linearly serrated Fourier filter may a symmetrically serrated Fourier filter. Linear serrations may or may not be ideal in terms of performance but may be most practical in terms of ease of fabrication. The performance degradation due to simple linear serrations will be acceptable for most applications.

A linearly periodically serrated Fourier filter has the following energy distribution in its transition region: 50% transmitted, 50% absorbed. Among the 50% transmitted energy, 33% goes to the zeroth diffraction order and 17% goes into higher diffraction orders.

Diffraction of a linearly serrated Fourier filter can be easily calculated by first separating the non-diffracting component from the whole transmitted wavefront (according to Babinet's principle), as shown in FIG. 7. The filter function of a linearly serrated Fourier filter can be described by the following equation:

$$\text{Filter function} = 1 - \left(1 + \frac{a}{b}\right) tri\left(\frac{y}{a+b}\right) + \frac{a}{b} tri\left(\frac{y}{a}\right) \quad (30)$$

whose Fourier transform is:

$$= \delta(f_y) - \left(1 + \frac{a}{b}\right)(a+b)\text{sinc}^2((a+b)f_y) + \frac{a^2}{b}\text{sinc}^2(af_y) \quad (31)$$

$$= \delta(f_y) - \left(1 + \frac{a}{b}\right)(a+b)\left[\frac{\sin(\pi(a+b)f_y)}{\pi(a+b)f_y}\right]^2 + \frac{a^2}{b}\left[\frac{\sin(\pi a f_y)}{\pi a f_y}\right]^2 \quad (32)$$

$$= \delta(f_y) - \frac{1}{2\pi^2 b f_y^2}(1 - \cos(2\pi(a+b)f_y)) + \frac{1}{2\pi^2 b f_y^2}(1 - \cos(2\pi a f_y)) \quad (33)$$

$$= \delta(f_y) - \frac{1}{2\pi^2 b f_y^2}[(1 - \cos(2\pi b f_y))\cos(2\pi a f_y) + \sin(2\pi a f_y)\sin(2\pi b f_y)] \quad (34)$$

$$= \delta(f_y) - b\left[\frac{\sin(\pi b f_y)}{\pi b f_y}\right]^2 - 2a\frac{\sin(2\pi a f_y)}{2\pi a f_y}\frac{\sin(2\pi b f_y)}{2\pi b f_y} \quad (35)$$

$$= \delta(f_y) - b\,\text{sinc}^2(bf_y) - 2a\,\text{sinc}(2af_y)\text{sinc}(2bf_y) \quad (36)$$

$$\approx \begin{cases} \delta(f_y) - b\,\text{sinc}^2(bf_y) & \text{as } a \to 0 \\ \delta(f_y) - 2a\,\text{sinc}(2af_y) & \text{as } b \to 0 \end{cases} \quad (37)$$

Figure 8:
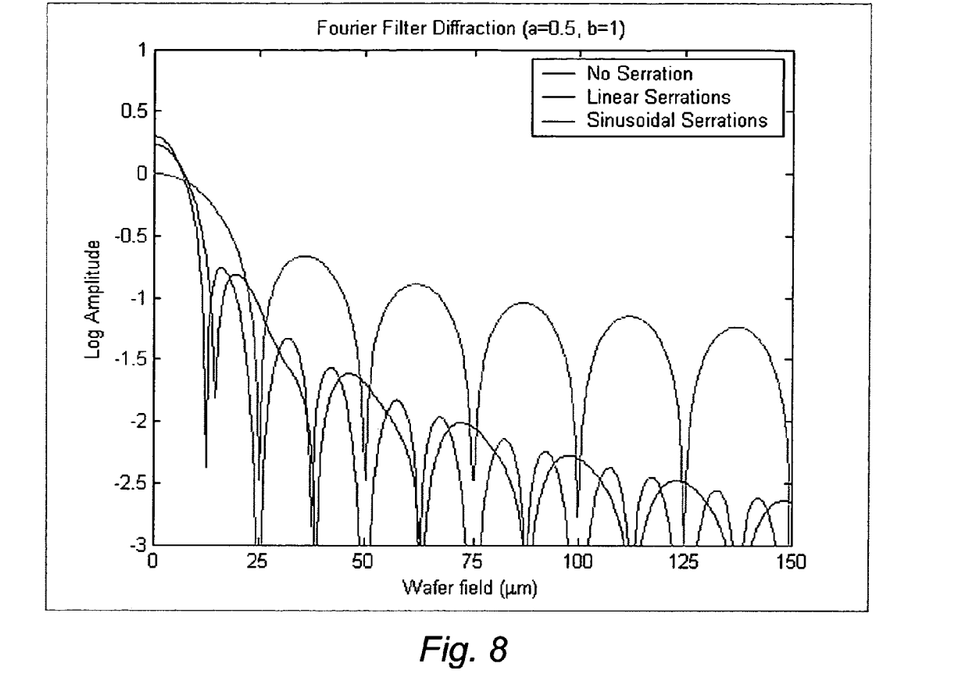
FIG. 8 is a plot illustrating diffraction patterns simulated for a Fourier filter that includes no serrations and different embodiments of Fourier filters that include periodic serrations having a 1.0 mm transition area width.

Numerical simulation can be used to compare the performance of a linearly periodically serrated Fourier filter with the performance of a sinusoidally periodically serrated Fourier filter and a Fourier filter with no serrations. Equations (27) and (34) are used for the calculations. FIG. 8 illustrates diffraction patterns simulated for Fourier filters having no serration, linear periodic serrations, or sinusoidal periodic serrations with a 1.0 mm transition area width (b, which is shown in FIGS. 3 and 6) and a=0.5 mm (a is also shown in FIGS. 3 and 6).

log amplitude is plotted on the y-axis of the graph shown in FIG. 8. The log amplitude is generally representative of noise. The noise across the wafer field is shown in FIG. 8, which is plotted along the x-axis (the x-axis shown in FIGS. 8-10 corresponds to y-axis on the wafer). In this manner, the plot of FIG. 8 illustrates how much light can be expected beyond individual pixels in the sensor array. As such, high log amplitude values in FIG. 8 are indicative of a large amount of light spilling over from one pixel to the next, which is obviously undesirable. Therefore, lower values of log amplitude in FIG. 8 indicate better performance.

The plot for a Fourier filter having no serrations is the plot in FIG. 8 that has much higher values of log amplitude at higher wafer field distances. The plot for a Fourier filter having sinusoidal periodic serrations is the plot that has much lower values of log amplitude at higher wafer field distances, particularly compared to the values for a Fourier filter having no serrations, and relatively wide peaks. The plot for a Fourier filter having linear periodic serrations is the plot that also has much lower values of log amplitude at higher wafer field distances but narrower peaks.

The numerical simulation results shown in FIG. 8 illustrate that a sinusoidally periodically serrated Fourier filter performs a little better than a linearly periodically serrated Fourier filter. However, the results shown in FIG. 8 also illustrate that the performance of a linearly serrated Fourier filter is very acceptable. In addition, the performance of a sinusoidally serrated Fourier filter and a linearly serrated Fourier filter are both substantially better than a Fourier filter having no serrations.

Figure 9:
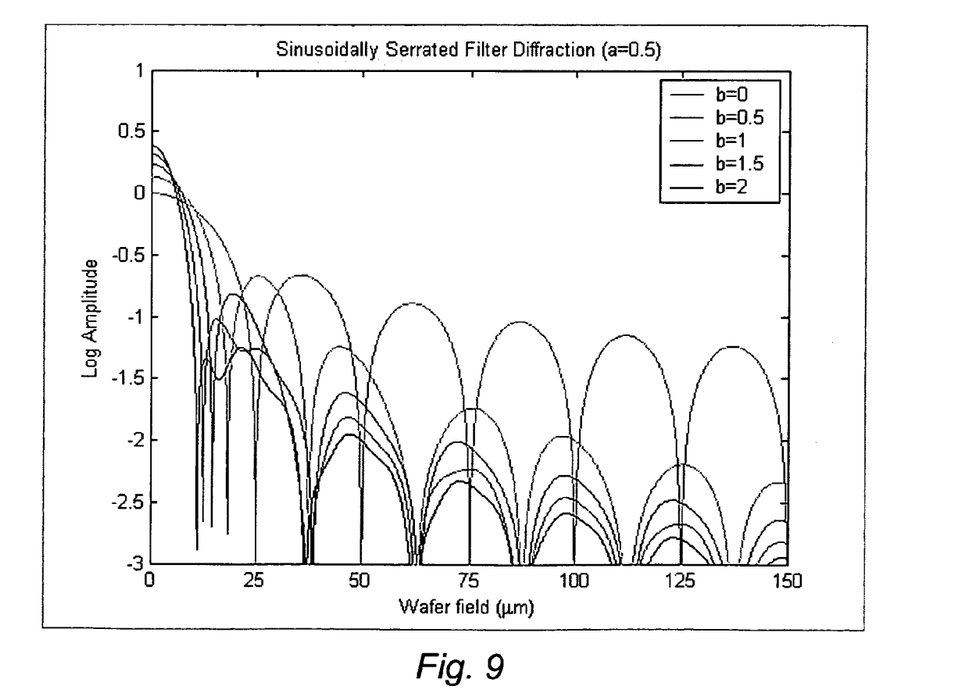
FIG. 9 is a plot illustrating diffraction patterns simulated for Fourier filters that include periodic serrations having different transitions area widths and a periodic serration width that varies sinusoidally along a length of the periodic serrations.
Figure 10:
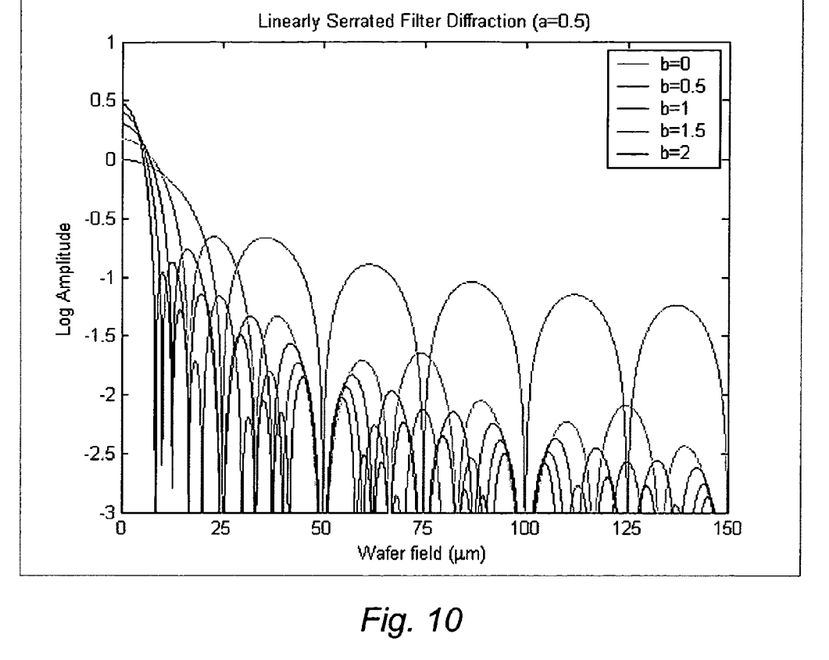
FIG. 10 is a plot illustrating diffraction patterns simulated for Fourier filters that include periodic serrations having different transition area widths and a periodic serration width that varies linearly along a length of the periodic serrations.

In some embodiments, the periodic serrations are configured to substantially reduce diffraction of zeroth order light into neighboring photosensitive elements (e.g., pixels of a detector or a sensor array) at an image plane. In this manner, the periodic serrations reduce the amount of interference produced at the image plane. In an additional embodiment, the periodic serrations are configured to prevent a substantial reduction in the signal-to-noise ratio of light transmitted by the Fourier filter. As such, the Fourier filters described herein can be used in optical applications in which high signal-to-noise ratios and therefore high sensitivity are desirable. For example, FIG. 9 illustrates diffraction patterns simulated for Fourier filters having sinusoidal periodic serrations with different transition area widths (b=0 mm, 0.5 mm, 1 mm, 1.5 mm, and 2 mm) and a=0.5 mm. FIG. 10 illustrates diffraction patterns simulated for Fourier filters having linear periodic serrations with different transition area widths (b=0 mm, 0.5 mm, 1 mm, 1.5 mm, and 2 mm) and a=0.5 mm.

Like FIG. 8, FIGS. 9 and 10 illustrate log amplitude vs. wafer field. In this manner, like the plots of FIG. 8, the plots of FIGS. 9 and 10 illustrate how much light can be expected beyond individual pixels in the sensor array. As such, high log amplitude values in FIGS. 9 and 10 are indicative of a large amount of light spilling over from one pixel to the next, which is obviously undesirable. Therefore, lower values of log amplitude in FIGS. 9 and 10 indicate better performance.

The numerical simulation results shown in FIGS. 9 and 10 illustrate that as the width of the transition region increases, the diffraction produced by the periodically serrated Fourier filter decreases. However, the results shown in FIGS. 9 and 10 also illustrate that the reward for an increased transition region width diminishes after a certain width. In particular, the plots with the highest log amplitude values in FIGS. 9 and 10 are for a Fourier filter having zero transition area width (i.e., a Fourier filter that has no serrations). In addition, as shown in FIGS. 9 and 10, as the transition area width is increased, the log amplitude values decrease. Furthermore, the decreases in the log amplitude values from the plot for b=0 mm compared to b=0.5 mm are relatively large. However, further increases in the transition area width do not yield equally large decreases in the log amplitude values. As such, as the transition area width increases beyond 0.5 mm, the reward in reduction in spillover decreases. In this manner, a Fourier filter that includes periodically serrated edges may be configured to have a transition region width that is large enough to reduce the diffraction of zeroth order light into neighboring areas to an acceptable level, but without blocking too much signal light. In other words, the transition area width can be selected to balance the tradeoff between noise and signal, both of which decrease as transition area width increases.

The Fourier filters described herein can be manufactured using any method and/or technique known in the art. For example, each of the blocking elements of a Fourier filter may be manufactured from a relatively thin metal plate. The metal plate may have a thickness of about 10 μm to about 0.1 mm. In addition, the metal plate may be formed of any suitable material known in the art. The blocking elements may be formed from the metal plate using any technique known in the art.

The periodically serrated Fourier filters described herein can be used in wafer inspection tools. In addition, the Fourier filters described herein can be used in any optical system known in the art that is or can be configured for wafer inspection or inspection of any other object having repetitive, strongly scattering, features.

In one embodiment, an inspection system configured to detect defects on a wafer includes a Fourier filter that includes periodic serrations formed on edges of one or more blocking elements. The one or more blocking elements are configured to block a portion of light returned from the wafer. The periodic serrations define a transition region of the one or more blocking elements. The periodic serrations are configured to vary transmission across the transition region such that variations in the transmission across the transition region are substantially smooth. The Fourier filter may be further configured as described and illustrated herein. The inspection system also includes a detector that is configured to detect light transmitted by the Fourier filter. Signals generated by the detector can be used to detect the defects on the wafer.

Figure 11:
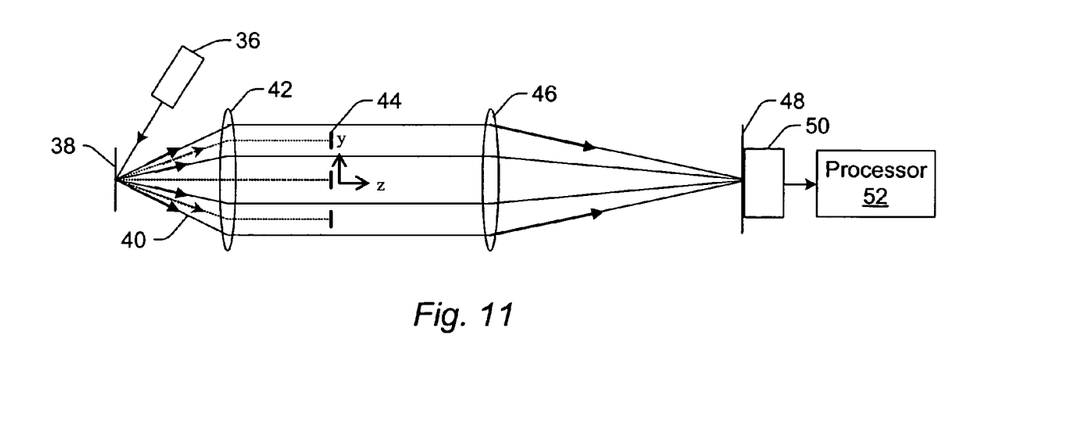
FIG. 11 is a schematic diagram illustrating a side view of one embodiment of an inspection system.

One embodiment of such an inspection system is illustrated in FIG. 11. As shown in FIG. 11, the inspection system includes light source 36. Light source 36 may include any suitable light source known in the art such as a laser configured to generate light having one or more wavelengths in the visible and/or ultraviolet range. Light source 36 is configured to direct light to object plane 38 at which a wafer (not shown) may be positioned. In addition, the inspection system may include one or more optical components (not shown) such as lenses, folding mirrors, polarizing components, etc., which are coupled to light source 36 and are configured to direct light from the light source to object plane 38.

Light 40 scattered and/or diffracted from object plane 38 is collected by collection lens 42. Collection lens 42 may include any suitable refractive or reflective component known in the art. Light collected by collection lens 42 passes through a Fourier plane of the system at which Fourier filter 44 is positioned. Fourier filter 44 may be configured as described herein. In particular, Fourier filter 44 includes periodic serrations formed on the edges of one or more blocking elements.

Light that is transmitted by the Fourier filter is focused by imaging lens 46 onto image plane 48 at which detector 50 is positioned. Imaging lens 46 may include any suitable refractive or reflective component known in the art. Detector 50 may include any suitable detector known in the art such as a linear array of photosensitive elements or an array detector such as a charge coupled device (CCD). In one embodiment, a period of the periodic serrations of the Fourier filter is selected such that all diffraction orders other than zeroth order are directed outside of the photosensitive elements of the detector. In an additional embodiment, the periodic serrations of the Fourier filter are configured to substantially reduce diffraction of zeroth order light into neighboring photosensitive elements (e.g., pixels) of the detector.

Signals generated by detector 50 in response to light detected by the detector may be provided to processor 52. Processor 52 may be coupled to detector 50 in any manner known in the art (e.g., by a transmission medium and/or one or more electronic components). Processor 52 may be configured to use the signals generated by the detector to detect defects on the wafer. The defects that may be detected using such a system include any type of defects that may be found on a wafer or another object being inspected. The processor may be configured to detect defects on the wafer using any method and/or technique known in the art. In addition, the processor may be configured to perform any other inspection-related functions known in the art (e.g., determining defect position, defect size, etc.). The processor may include any appropriate processing component known in the art such as a processor of a computer system.

Although one particular configuration of a wafer inspection system is shown in FIG. 11, it is to be understood that the Fourier filters described herein may be used in any optical wafer inspection system known in the art. As described herein, the Fourier filters may be positioned at the Fourier plane of any other optical wafer inspection system known in the art.

Further modifications and alternative embodiments of various aspects of the invention may be apparent to those skilled in the art in view of this description. For example, serrated Fourier filters and inspection systems are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A Fourier filter configured to block a portion of light from a wafer, comprising:
   one or more blocking elements configured to block the portion of the light; and
   periodic serrations formed on edges of the one or more blocking elements, wherein the periodic serrations define a transition region of the one or more blocking elements, and wherein the periodic serrations are configured to vary transmission across the transition region such that variations in the transmission across the transition region are substantially smooth.

2. The Fourier filter of claim 1, wherein a period of the periodic serrations is selected such that all diffraction orders other than zeroth order are directed outside of photosensitive elements at an image plane.

3. The Fourier filter of claim 1, wherein the periodic serrations are further configured to substantially reduce diffraction of zeroth order light into neighboring photosensitive elements at an image plane.

4. The Fourier filter of claim 1, wherein the periodic serrations are further configured to prevent a substantial reduction in signal-to-noise ratio of light transmitted by the Fourier filter.

5. The Fourier filter of claim 1, wherein the transmission is an average transmission.

6. The Fourier filter of claim 1, wherein the variations in the transmission comprise one or more local transmission minima.

7. The Fourier filter of claim 1, wherein a width of the periodic serrations varies approximately sinusoidally across a length of the periodic serrations.

8. The Fourier filter of claim 1, wherein a width of the periodic serrations varies approximately linearly across a length of the periodic serrations.

9. The Fourier filter of claim 1, wherein the periodic serrations are arranged symmetrically along the edges of the one or more blocking elements.

10. The Fourier filter of claim 1, wherein the periodic serrations are arranged asymmetrically along the edges of the one or more blocking elements.

11. A Fourier filter configured to block a portion of light from a wafer, comprising one or more blocking elements configured to block the portion of the light, wherein the one or more blocking elements have a transition region across which transmission varies, wherein the transition region is not physically smooth due to periodic serrations formed on edges of the one or more blocking elements, and wherein the transition region is substantially optically smooth.

12. An inspection system configured to detect defects on a wafer, comprising:
 a Fourier filter comprising periodic serrations formed on edges of one or more blocking elements, wherein the one or more blocking elements are configured to block a portion of light returned from the wafer, wherein the periodic serrations define a transition region of the one or more blocking elements, and wherein the periodic serrations are configured to vary transmission across the transition region such that variations in the transmission across the transition region are substantially smooth; and
 a detector configured to detect light transmitted by the Fourier filter, wherein signals generated by the detector can be used to detect the defects on the wafer.

13. The system of claim 12, wherein a period of the periodic serrations is selected such that all diffraction orders other than zeroth order are directed outside of photosensitive elements of the detector.

14. The system of claim 12, wherein the periodic serrations are further configured to substantially reduce diffraction of zeroth order light into neighboring photosensitive elements of the detector.

15. The system of claim 12, wherein the periodic serrations are further configured to prevent a substantial reduction in signal-to-noise ratio of the light transmitted by the Fourier filter.

16. The system of claim 12, wherein the transmission is an average transmission.

17. The system of claim 12, wherein the variations in the transmission comprise one or more local transmission minima.

18. The system of claim 12, wherein a width of the periodic serrations varies approximately sinusoidally across a length of the periodic serrations.

19. The system of claim 12, wherein a width of the periodic serrations varies approximately linearly across a length of the periodic serrations.

20. The system of claim 12, wherein the periodic serrations are arranged symmetrically along the edges of the one or more blocking elements.

21. The system of claim 12, wherein the periodic serrations are arranged asymmetrically along the edges of the one or more blocking elements.

* * * * *